United States Patent

Nakanishi et al.

[11] 3,974,168
[45] Aug. 10, 1976

[54] TRICYCLE SUBSTITUTED ACETONES

[75] Inventors: Michio Nakanishi; Takanori Oe, both of Nakatsu; Mineo Tsuruda, Fukuoka, all of Japan

[73] Assignee: Yoshitomi Pharmaceutical Industries, Ltd., Osaka, Japan

[22] Filed: Sept. 4, 1974

[21] Appl. No.: 503,207

[30] Foreign Application Priority Data
Sept. 4, 1973  Japan.................................. 48-99828
Nov. 5, 1973  Japan.............................. 48-124840

[52] U.S. Cl. ............................ 260/295 T; 424/256; 424/258; 260/294.8 B; 260/296 T; 260/297 T
[51] Int. Cl.²................ C07D 487/00; C07D 491/92
[58] Field of Search......... 260/297 T, 295 T, 296 T, 260/294.8 B

[56] References Cited
UNITED STATES PATENTS

| | | | |
|---|---|---|---|
| 3,803,153 | 4/1974 | Villani | 260/293.53 |
| 3,931,199 | 1/1976 | Nakanishi et al. | 260/294.8 B |
| 3,931,205 | 1/1976 | Nakanishi et al. | 260/295 T |

FOREIGN PATENTS OR APPLICATIONS

| | | | |
|---|---|---|---|
| 2,337,052 | 2/1974 | Germany | 260/297 T |

OTHER PUBLICATIONS

Conant, The Chemistry of Carbon Compounds, frontispiece and pp. 243 to 244, The Macmillan Co., Sixth printing 1943 (NY).
Wegland, Organic Preparations, frontispiece and pp. 445–450, 464 to 465, Interscience Publishers, Inc. NY (1945).
Mann et al., Chemical Abstracts, vol. 47, cols. 1157 to 1158 (1953).

*Primary Examiner*—John D. Randolph
*Attorney, Agent, or Firm*—Sughrue, Rothwell, Mion, Zinn & Macpeak

[57] ABSTRACT

Compounds of the formula:

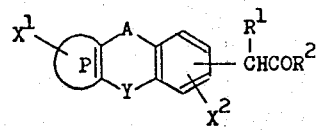

wherein
of $X^1$ and $X^2$ is a hydrogen atom, a halogen atom or an alkyl group having 1 to 4 carbon atoms;
$R^1$ is a hydrogen atom, an alkyl group having 1 to 4 carbon atoms, an alkenyl group having 2 to 4 carbon atoms, an alkynyl group having 2 to 4 carbon atoms or a group $-B^1-R^3$ (wherein $B^1$ is an alkylene group having 1 to 4 carbon atoms, and $R^3$ is a carboxyl group, an alkoxycarbonyl group in which the alkoxy moiety has 1 to 4 carbon atoms, an alkoxy group having 1 to 4 carbon atoms or a di-alkyl-amino group in which each alkyl moiety has 1 to 4 carbon atoms);
$R^2$ is an alkyl group having 1 to 4 carbon atoms or a group $-B^2-R^4$ (wherein $B^2$ is an alkylene group having 2 to 4 carbon atoms, and $R^4$ is a carboxyl group or a di-alkyl-amino group in which each alkyl moiety has 1 to 4 carbon atoms);
A is a methylene group or a carbonyl group;
Y is an oxygen atom, a sulfur atom or an alkyl-imino group in which the alkyl moiety has 1 to 4 carbon atoms; and
ring P is a pyridine ring; and
pharmaceutically acceptable salts thereof are disclosed.

They are useful as anti-inflammatory agents, analgesics, antipyretics and antirheumatics.

23 Claims, No Drawings

TRICYCLE SUBSTITUTED ACETONES

This invention relates to tricycle substituted acetones of the formula:

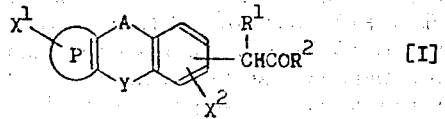

and pharmaceutically acceptable salts thereof, wherein each of $X^1$ and $X^2$ is a hydrogen atom, a halogen atom or an alkyl group having 1 to 4 carbon atoms; $R^1$ is a hydrogen atom, an alkyl group having 1 to 4 carbon atoms, an alkenyl group having 2 to 4 carbon atoms, an alkynyl group having 2 to 4 carbon atoms or a group $-B^1-R^3$ (wherein $B^1$ is an alkylene group having 1 to 4 carbon atoms, and $R^3$ is a carboxyl group, an alkoxycarbonyl group in which the alkoxy moiety has 1 to 4 carbon atoms, an alkoxy group having 1 to 4 carbon atoms or a di-alkyl-amino group in which each alkyl moiety has 1 to 4 carbon atoms); $R^2$ is an alkyl group having 1 to 4 carbon atoms or a group $-B^2-R^4$ (wherein $B^2$ is an alkylene group having 2 to 4 carbon atoms, and $R^4$ is a carboxyl group or a di-alkyl-amino group in which each alkyl moiety has 1 to 4 carbon atoms);
A is a methylene group or a carbonyl group;
Y is an oxygen atom, a sulfur atom or an alkyl-imino group in which the alkyl moiety has 1 to 4 carbon atoms; and
ring P is a pyridine ring.

In the above definition, the alkyl group or moiety includes methyl, ethyl, propyl, isopropyl and butyl; the alkenyl group includes vinyl, allyl, isopropenyl and 2-butenyl; the alkynyl group includes ethynyl, 2-propynyl and 2-butynyl; the alkoxy group or moiety includes methoxy, ethoxy, propoxy, isopropoxy and butoxy; the alkylene group includes methylene, ethylene, trimethylene, propylene and tetramethylene; and the halogen atom includes F, Cl and Br.

The ring system:

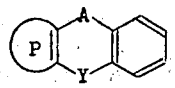

in the above formula [I] and also hereinafter represents any of the following structures (1)–(4).

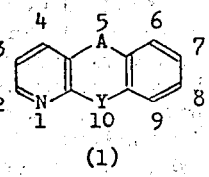

(1)

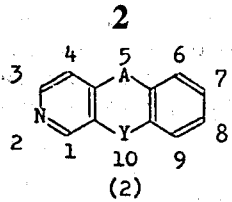

(2)

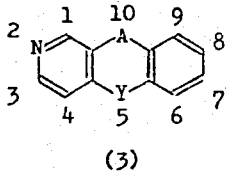

(3)

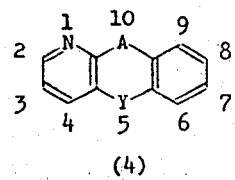

(4)

The compounds of formula [I] can be produced, for example, by the following methods (a) and (b):

a. By decarboxylating following hydrolyzing a compound of the formula:

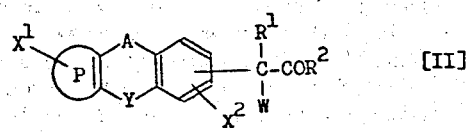

wherein W is a functional group hydrolyzable to a carboxyl group (e.g. alkoxycarbonyl, cyano, carbamoyl or

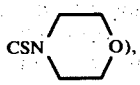

and other symbols are as defined above and in addition $R^4$ (in the group $-B^2-R^4$ which $R^2$ stands for) may further be an alkoxycarbonyl group in which the alkoxy moiety has 1 to 4 carbon atoms.

In case where, in formula [II], $R^1$ is a group $-B^1-R^3$ and $R^3$ is an alkoxycarbonyl group and/or where $R^2$ is a group $-B^2-R^4$ and $R^4$ is an alkoxycarbonyl group, each alkoxycarbonyl group is simultaneously hydrolyzed to a carboxyl group.

The reaction is carried out in a conventional manner; for example, the starting compound of formula [II] is hydrolyzed under alkaline conditions with sodium hydroxide, potassium hydroxide, sodium carbonate or potassium carbonate, and the thus-obtained carboxylic acid is decarboxylated under neutral or acid conditions; or more preferably, the starting compound is hydrolyzed and decarboxylated at a single stroke under acid conditions with hydrochloric, sulfuric, phosphoric or hydrobromic acid. The reaction is usually carried out at 10°–200°C for 3–60 hours, if necessary, in an inert solvent such as water, acetic acid, methanol, ethanol, dioxane, acetone or a mixture thereof.

b. By reacting a compound of the formula:

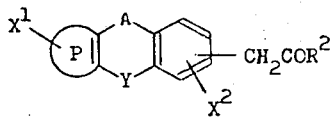 [III]

wherein each symbol is as defined above, with a compound of the formula:

R¹—Z [IV]

wherein $R^1$ is as above defined except that it does not represent a hydrogen atom and Z is a reactive atom or group (e.g. halogen atom such as Cl, Br or I or alkyl- or aryl-sulfonyloxy such as methylsulfonyloxy or p-tolylsulfonyloxy).

The reaction is usually carried out in a solvent (e.g. methanol, ethanol, isopropyl alcohol, butanol, acetone, methyl ethyl ketone, cyclohexanone, benzene, toluene, xylene, ethyl ether, tetrahydrofuran, dimethyl sulfoxide, dimethylformamide, liquid ammonia, water or a mixture thereof), if necessary, in the presence of a condensing agent (e.g. sodium hydroxide, potassium hydroxide, sodium methoxide, sodium ethoxide, potassium t-butoxide, sodium amide or sodium hydride) at a temperature of from 10° to 150°C for a period of from 10 minutes to 2 hours.

The compounds of formula [I], where they bear a carboxyl group, can be converted in a conventional manner into the corresponding metal salts such as Na, K, Ca and Al salts, into the corresponding ammonium salts and into the corresponding organic base addition salts such as dimethylamine and triethylamine salts, and, when they bear a di-alkyl-amino group, can be converted into the corresponding inorganic or organic salts such as hydrochloride, sulfate, hydrobromide, maleate, fumarate and tartrate.

The compounds of formual [I] and pharmaceutically acceptable salts thereof can be administered safely as anti-inflammatory agents, analgesics, antipyretics and antirheumatics, in the form of a pharmaceutical composition consisting essentially of a therapeutically effective amount of the compound in admixture with a suitable and conventional carrier or adjuvant, administrable orally, percutaneously or by way of injection, without harm to the host.

The pharmaceutical preparations can take any conventional form such as tablets, capsules, granules, powders, injectable solutions, creams, etc.

The daily dose of compound [I] or a pharmaceutically acceptable salt thereof for human adults ranges from 300 to 600 mg for oral administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

24 g of 5H-[1]benzopyrano[2,3-b]pyridin-7-yl-acetone is dissolved in a solution of 2.5 g of metallic sodium in 120 ml of isopropyl alcohol at 50°–60°C with stirring. The solution is cooled to 40°C with water, 17.2 g of methyl iodide is added, and the mixture is stirred under reflux for 1 hour. The isopropyl alcohol is distilled off under reduced pressure, and the residue is dissolved in chloroform. After water cooling, the solution is dried over anhydrous magnesium sulfate and concentrated, and the residue is recrystallized from isopropyl alcohol to give 19 g of 3-(5H-[1]benzopyrano[2,3-b]pyridin-7-yl)-2-butanone melting at 136°–136°C.

EXAMPLE 2

3 g of 5H-[1]benzopyrano[2,3-b]pyridin-7-yl-acetone is dissolved in a solution of 0.32 g of metallic sodium in 15 ml of absolute isopropyl alcohol by warming to 50°–60°C. The solution is cooled to 40°C, 3.5 g of 2-methoxyethyl p-toluenesulfonate is added, and the mixture is stirred under reflux for 1.5 hours. The reaction mixture is concentrated, chloroform and water are added to the residue, and the mixture is stirred. The chloroform layer is separated, dried over anhydrous magnesium sulfate and concentrated. The oily residue is column chromatographed over silica gel (100 g) with a mixture of chloroform and ethyl acetate (10:1) as eluent to give 2.0 g of 3-(5H-[1]benzopyrano[2,3-b]pyridin-7-yl)-5-methoxy-2-pentanone as a pale yellow transparent oil. $n_D^{28} = 1.5764$

EXAMPLE 3

4.1 g of 5H-[1]benzopyrano[2,3-b]pyridin-7-yl-acetone is dissolved in a solution of 0.44 g of metallic sodium in 20 ml of absolute isopropyl alcohol by warming to 50°–60°C. The solution is water-cooled, 2.3 g of 2-dimethylaminoethyl chloride is added, and the mixture is stirred under reflux for 1 hour. The reaction mixture is concentrated, chloroform and water are added to the residue, and the mixture is shaken. The chloroform layer is separated and extracted with dilute hydrochloric acid, and the extract is neutralized with 10% sodium hydroxide and then extracted with chloroform. The chloroform extract is washed with water, dried over anhydrous magnesium sulfate and concentrated to give 3 g of crude 3-(5H-[1]benzopyrano[2,3-b]-pyridin-7-yl)-5-dimethylamino-2-pentanone as a pale yellowish brown transparent oil. The product is treated with maleic acid in acetone in a conventional manner, and the crystalline precipitate is recrystallized from isopropyl alcohol to give 3-(5H-[1]benzopyrano[2,3-b]pyridin-7-yl)-5-dimethylamino-2-pentanone maleate as white needles melting at 145°–146°C.

EXAMPLE 4

2.2 g of 3-(5H-[1]benzopyrano[2,3-b]pyridin-7-yl)-3-cyano-2-butanone is dissolved in 5 ml of concentrated sulfuric acid. 15 ml of water is added at a stretch to the solution with stirring under ice-cooling, and the mixture is stirred under reflux for 5 hours. The reaction mixture is ice-cooled and neutralized by adding 30% sodium hydroxide with stirring. The crystalline precipitate is filtered off, dried and recrystallized from isopropyl alcohol to give 1.6 g of 3-(5H-[1]benzopyrano[[2,3-b]pyridin-7-yl)-2-butanone melting at 136°–137°C.

EXAMPLE 5

4.8 g of ethyl 5(5H-[1]benzopyrano[2,3-b]pyridin-7-yl)-5-cyano-4-oxovalerate is dissolved in 10 ml of concentrated hydrochloric acid. 30 ml of water is added at a stretch to the solution with stirring under ice-cooling, and the mixture is stirred under reflux for 5 hours. The reaction mixture is ice-cooled and adjusted to approximately pH 3 by addition of 30% sodium hydroxide. The resulting oil layer is extracted with chloroform, and the extract is dried over anhydrous sodium sulfate and concentrated. The oily residue, on standing, becomes solid. The solid is recrystallized from a mixture of dioxane and water (1:1) to give 3.4 g of 5-(5H-[1]benzopyrano[2,3-b]pyridin-7-yl)-4-oxovaleric acid as white needles melting at 146°–147°C.

EXAMPLE 6

11 g of 1-(5H-[1]benzopyrano[2,3-b]pyriding-7-yl)-1-cyano-5-dimethylamino-2-pentanone is dissolved in a mixture of 33 ml of concentrated hydrochloric acid and 66 ml of acetic acid, and the solution is refluxed for 60 hours. The reaction mixture is concentrated under reduced pressure, and the residue is dissolved in water. The solution is alkalified with potassium carbonate, and the resulting oil layer is extracted with benzene. The extract is dried and concentrated, and the residue is recrystallized from a mixture of n-hexane and benzene to give 7.5 g of 1-(5H-[1]benzopyrano[2,3-b]pyridin-7-yl)-5-dimethylamino-2-pentanone melting at 76°–78°C. The corresponding maleate, when recrystallized from acetone, melts at 117°C.

Using the procedure set forth in the above examples, but substituting equivalent amount of the appropriate starting material, the following compounds are also produced:

1. 5H-[1]benxopyrano[2,3-b]pyridin-7-yl-acetone, melting at 124°–125°C;
2. 5-oxo-5H-[1]benzopyrano[2,3-b]pyridin-7-yl-acetone, melting at 173°–174°C;
3. 2-methyl-5H-[1]benzopyrano[2,3-b]pyridin-7-yl-acetone, melting at 107°–108°C;
4. 9-chloro-5H-[1]benzopyrano[2,3-b]pyridin-7-yl-acetone;
5. 3-(5-oxo5H-[1]benzopyrano[2,3-b]pyridin-7-yl)-2-butanone, melting at 193.5°–194°C;
6. 3-(5H-[1]benzothiopyrano[2,3-b]pyridin-7-yl)-2-butanone, $n_D^{28} = 1.6267$;
7. 3-(10-methyl-5H,10H-benzo[b][1,8]naphthyridin-7-yl)-2-butanone;
8. 3-(2-methyl-5H-[1]benzopyrano[2,3-b]pyridin-7-yl)-2-butanone, melting at 134°–135.5°C;
9. 1-(5H-[1]benzopyrano[2,3-b]pyridin-7-yl)-2-butanone, melting at 100°–101.5°C;
10. 1-(5H-[1]benzopyrano[2,3-b]pyridin-7-yl)-3-methyl-2-butanone, melting at 92°–93.5°C;
11. 2-(5H-[1]benzopyrano[2,3-b]pyridin-7-yl)-3-pentanone, $n_D^{27.5} = 1.5830$;
12. 2-(5H-[1]benzopyrano[2,3-b]pyridin-7-yl)-4-methyl-3-pentanone, $n_D^{27.5} = 1.5696$;
13. 3-(5H-[1]benzopyrano[2,3-b]pyridin-7-yl)-5-hexen-2-one, $n_D^{27.5} = 1.5852$;
14. 3-(5H-[1]benzopyrano[2,3-b]pyridin-7-yl)-5-hexyn-2-one, melting at 132°–133.5°C;
15. 3-(5H-[1]benzopyrano[2,3-b]pyridin-7-yl)-4-oxovaleric acid, melting at 206°–208°C;
16. 5-(5H-[1]benzopyrano[2,3-b]pyridin-7-yl)-4-oxohexanoic acid; melting at 153°–154°C;
17. ethyl 3-(5H-[1]benzopyrano[2,3-b]pyridin-7-yl)-4-oxovalerate, melting at 104°–105°C.

Pharmacological Test

The compounds of the present invention exhibit anti-inflammatory and analgesic actions as shown, for example, by the following tests:

Anti-inflammatory Action i. Carrageenin Edema Method

According to the method of Winter et al. (Proc. Soc. Exptl. Biol. Med., 111, 544 (1962)), to one group of five Donryu-strain male rats each weighing about 130 g a test solution containing a test compound was administered orally. One hour later 0.05 ml of 1% carrageenin solution as a phlogogenic substance was subcutaneously injected to the paw of the hind leg. And 2 hours after the administration of phlogogen the bulk of the paw was measured in order to obtain the increment percentage over that before administration. The ratio of bulk increment between a control group and a test group was calculated as inhibition percentage.

ii. Ultraviolet Erythema Method

Using guinea pigs weighing 250–450 g, a rubber plate with 3 holes of 7 mm in diameter was fitted to the abdomen, hair of which had been removed in advance, and light was given by a mercury lamp (300 W) at the distance of 15 cm for 150 seconds. Two hours later the degree of erythema formation was marked according to the method of Winder et al. (Arch. Intern. Pharmacodyn., 116, 261 (1958)) and the efficacy rate was calculated, based on the criterion that 1.5 or less of total marks be effective. Half amount of the test solution was orally given 1 hour before and after the irradiation.

Analgesic Action (Phenylquinone Method)

According to the method of Hendershot et al. (J. Pharmacol. Exptl. Therap., 125, 237 (1957)), to one group of six dd-strain male mice each weighing about 20 g a test solution containing a test compound was orally administered and 1 hour later 0.2 ml/20 g of body weight of 0.02% o-phenyl-p-benzoquinone solution was intraperitoneally injected. The frequency of stretch symptoms thus induced was measured for 30 minutes, and compared with that of a control group, and the inhibition percentage (effect) was calculated. Results:

| Compound | Carrageenin Edema Method Dose (mg/kg) p.o. | % inhibition |
|---|---|---|
| A | 5 | 50 |
|  | 25 | 68 |
| B | 10 | 36 |
|  | 25 | 61 |
| C | 25 | 32 |
|  | 50 | 63 |

| | Ultraviolet Erythema Method | Animals with score of 1.5 or less |
|---|---|---|
| Compound | Dose (mg/kg) p.o. | Total animals |
| A | 1 | 3/10 |
|  | 2.5 | 6/10 |

-continued
Ultraviolet Erythema Method

| Compound | Dose (mg/kg) p.o. | Animals with score of 1.5 or less / Total animals |
|---|---|---|
| B | 100 | 2/5 |
|   | 250 | 4/5 |
| C | 1 | 2/5 |
|   | 5 | 3/5 |

Phenylquinone Method

| Compound | Dose (mg/kg) p.o. | % inhibition |
|---|---|---|
| A | 5 | 48.7 |
|   | 10 | 73.5 |
| B | 0.5 | 24.0 |
|   | 1 | 63.4 |
| C | 25 | 41.6 |
|   | 50 | 75.2 |

Test Compounds
A. 3-(5H-[1]benzopyrano[2,3-b]pyridin-7-yl)-2-butanone
B. 3-(2-methyl-5H-[1]benzopyrano[2,3-b]pyridin-7-yl)-2-butanone
C. 2-(5H-[1]benzopyrano[2,3-b]pyridin-7-yl)-3-pentanone Formulation Examples The following is an example of formulations when a compound of the invention is administered for pharmaceutical purposes 100 mg tablets are prepared from the following compositions:

| Compound [A] | 100 mg |
| Lactose | 100 |
| Microcrystalline cellulose | 18 |
| Magnesium Stearate | 2 |
| Corn Starch | 30 |
|  | 250 mg |

100 mg capsules are prepared from the following compositions:

| Compound [A] | 100 mg |
| Lactose | 100 |
| Corn Starch | 50 |
| Talc | 10 |
|  | 260 mg |

Starting Materials

The starting materials can be produced, for example, by the following methods:

where Hal is a halogen atom.

A specific example of the preparation of [VI]

A solution of 7.8 g of potassium cyanide in 20 ml of water is added dropwise to a mixture of 23 g of 7-chloromethyl-5H-[1]benzopyrano[2,3-b]-pyridine and 200 ml of dimethylformamide, and the whole mixture is allowed to stand at 55°–60°C for 2 hours. The reaction mixture is poured into a large amount of water, and the crystalline precipitate is filtered off, washed with water and recrystallized from aqueous dioxane to give 20 g of 5H-[1]-benzopyrano[2,3-b]pyridin-7-yl-acetonitrile melting at 166°–167°C.

A specific example of the preparation of [IIa]

33 g of 5H-[1]benzopyrano[2,3-b]pyridin-7-yl-acetonitrile is suspended in 75 ml of ethyl acetate, a solution of 3.75 g of metallic sodium in 75 ml of absolute ethanol is added to the suspension, and the mixture is stirred under reflux for 1 hour. The reaction mixture is water-cooled, and crystals are filtered off, washed with ethyl acetate and dried to give 38 g of sodium salt of 1-(5H-[1]benzopyrano[2,3-b]pyridin-7-yl)-1-cyano-acetone melting at above 300°C. The sodium salt is dissolved in water, and the solution is acidified with acetic acid. The resulting gel substance is crystallized by warming, and the crystals are recrystallized from dimethylformamide to give 1-(5H-[1]benzopyrano[2,3-b]pyridin-7-yl)-1-cyano-acetone melting at 245°–248°C.

A specific example of the preparation of [IIb]

2.9 g of sodium salt of 1-(5H-[1]benzopyrano[2,3-b]pyridin-7-yl)-1-cyano-acetone is dissolved in 15 ml of dried dimethylformamide, 1.6 g of methyl iodide is added to the solution with stirring, and the mixture is stirred at room temperature for 1.5 hours. The reaction mixture is concentrated, and water is added to the oily residue. The crystalline precipitate is filtered off and recrystallized from ethanol to give 2.2 g of 3-(5H-[1]-benzopyrano[2,3-b]pyridin-7-yl)-3-cyano-2-butanone as white needles melting at 163.5°–164.5°C.

A specific example of the preparation of [IIIa]

1-(5H-[1]benzopyrano[2,3-b]pyridin-7-yl)-1-cyano-acetone prepared from 33 g of 5H-[1]benzopyrano[2,3-b]pyridin-7-yl-acetonitrile and 75 ml of ethyl acetate is added in small portions to 75 ml of concentrated sulfuric acid with stirring, while the temperature is maintained at below 20°C by cooling with

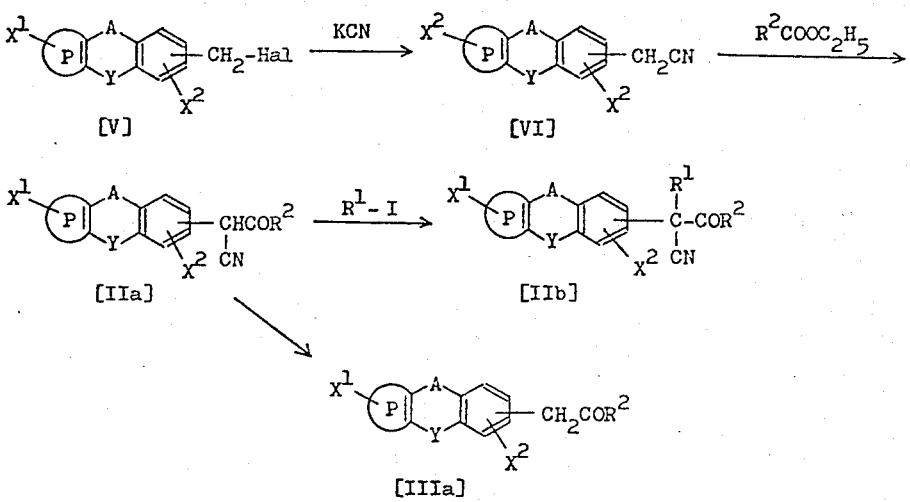

ice. 225 ml of water is added at a stretch to the mixture, and the whole mixture is stirred under reflux for 5 hours. The reaction mixture is ice-cooled and strongly alkalified by adding 30% sodium hydroxide with stirring. The crystalline precipitate is extracted with chloroform, and the extract is washed with water and dried over anhydrous sodium sulfate. The chloroform is distilled off, and the residue is recrystallized from isopropyl alcohol to give 25 g of 5H-[1]benzopyrano[2,3-b]pyridin-7-yl-acetone as white needles melting at 124°–125°C.

[V] are known compounds, and they can be produced, for example, by the following methods:

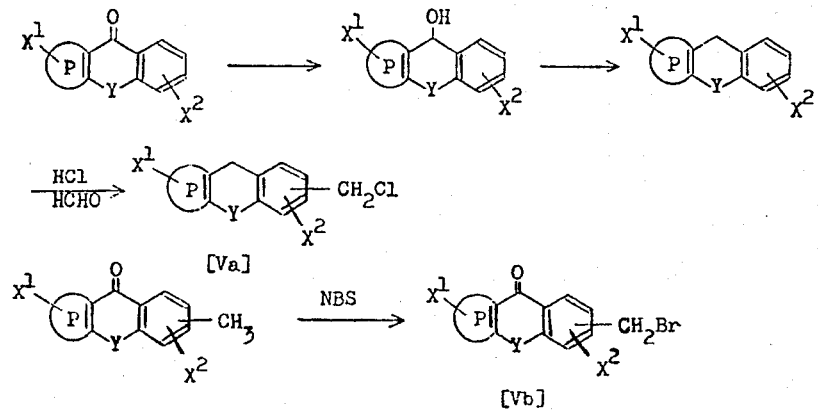

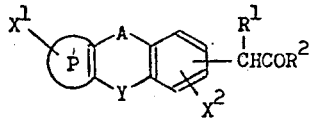

Although the present invention has been adequately discussed in the foregoing specifications and examples included therein, one readily recognizes that various changes and modifications may be made without departing from the spirit and scope thereof.

What is claimed is:

1. A compound of the formula:

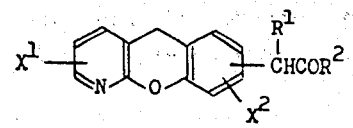

wherein each of $X^1$ and $X^2$ is a hydrogen atom, a halogen atom or an alkyl group having 1 to 4 carbon atoms;

$R^1$ is a hydrogen atom, an alkyl group having 1 to 4 carbon atoms, an alkenyl group having 2 to 4 carbon atoms, an alkynyl group having 2 to 4 carbon atoms or a group $-B^1-R^3$ (wherein $B^1$ is an alkylene group having 1 to 4 carbon atoms, and $R^3$ is a carboxyl group, an alkoxycarbonyl group in which the alkoxy moiety has 1 to 4 carbon atoms, an alkoxy group having 1 to 4 carbon atoms or a di-alkyl-amino group in which each alkyl moiety has 1 to 4 carbon atoms);

$R^2$ is an alkyl group having 1 to 4 carbon atoms or a group $-B^2-R^4$ wherein $B^2$ is an alkylene group having 2 to 4 carbon atoms, and $R^4$ is a carboxyl group or a di-alkyl-amino group in which each alkyl moiety has 1 to 4 carbon atoms);

A is a methylene group or a carbonyl group;

Y is an oxygen atom, a sulfur atom or an alkyl-imino group in which the alkyl moiety has 1 to 4 carbon atoms; and ring P is a pyridine ring; and a pharmaceutically acceptable salt thereof.

2. A compound of the formula:

wherein each of $X^1$ and $X^2$ is a hydrogen atom, a halogen atom or an alkyl group having 1 to 4 carbon atoms;

$R^1$ is a hydrogen atom or an alkyl group having 1 to 4 carbon atoms; and $R^2$ is an alkyl group having 1 to 4 carbon atoms; and a pharmaceutically acceptable salt thereof.

3. A compound of claim 1: 5H-[1]benzopyrano[2,3-b]pyridin-7-yl-acetone.

4. A compound of claim 1: 5-oxo-5H-[1]benzopyrano[2,3-b]pyridin-7-yl-acetone.

5. A compound of claim 1: 2-methyl-5H-[1]benzopyrano[2,3-b]pyridin-7-yl-acetone.

6. A compound of claim 1: 9-chloro-5H-[1]benzopyrano[2,3-b]pyridin-7-yl-acetone.

7. A compound of claim 1: 3-(5H-[1]benzopyrano[2,3-b]pyridin-7-yl)-2-butanone.

8. A compound of claim 1: 3-(5-oxo-5H-[1]benzopyrano[2,3-b]pyridin-7-yl)-2-butanone.

9. A compound of claim 1: 3-(5H-[1]benzothiopyrano[2,3-b]pyridin-7-yl)-2-butanone.

10. A compound of claim 1: 3-(2-methyl-5H-[1]benzopyrano[2,3-b]pyridin-7-yl)-2-butanone.

11. A compound of claim 1: 1-(5H-[1]benzopyrano[2,3-b]pyridin-7-yl)-2-butanone.

12. A compound of claim 1: 1-(5H-[1]benzopyrano[2,3-b]pyridin-7-yl)-3-methyl-2-butanone.

13. A compound of claim 1: 2-(5H-[1]benzopyrano[2,3-b]pyridin-7-yl)-3-pentanone.

14. A compound of claim 1: 2-(5H-[1]benzopyrano[2,3-b]pyridin-7-yl)-4-methyl-3-pentanone.

15. A compound of claim 1: 3-(5H-[1]benzopyrano[2,3-b]pyridin-7-yl)-5-hexen-2-one.

16. A compound of claim 1: 3-(5H-[1]benzopyrano[2,3-b]pyridin-7-yl)-5-hexyn-2-one.

17. A compound of claim 1: 3-(5H-[1]benzopyrano[2,3-b]pyridin-7-yl)-5-methoxy-2-pentanone.

18. A compound of claim 1: 3-(5H-[1]benzopyrano[2,3-b]pyridin-7-yl)-5-dimethylamino-2-pentanone.

19. A compound of claim 1: 1-(5H-[1]benzopyrano[2,3-b]pyridin-7-yl)-4-dimethylamino-2-butanone.

20. A compound of claim 1: 3-(5H-[1]benzopyrano[2,3-b]pyridin-7-yl)-4-oxovaleric acid.

21. A compound of claim 1: 5-(5H-[1]benzopyrano[2,3-b]pyridin-7-yl)-4-oxovaleric acid.

22. A compound of claim 1: 5-(5H-[1]benzopyrano[2,3-b]pyridin-7-yl)-4-oxohexanoic acid.

23. A compound of claim 1: ethyl 3-(5H-[1]benzopyrano[2,3-b]pyridin-7-yl)-4-oxovalerate.

* * * * *